United States Patent [19]

Riley

[11] 4,292,446

[45] Sep. 29, 1981

[54] ANILINE DERIVATIVES

[75] Inventor: Norman Riley, Manchester, England

[73] Assignee: Imperial Chemical Industries Limited, London, England

[21] Appl. No.: 168,513

[22] Filed: Jul. 14, 1980

Related U.S. Application Data

[63] Continuation of Ser. No. 935,498, Aug. 18, 1978, abandoned.

[30] Foreign Application Priority Data

Jan. 18, 1978 [GB] United Kingdom ................ 1991/78

[51] Int. Cl.$^3$ .................. C07C 102/00; C07C 85/153
[52] U.S. Cl. ............................. 564/221; 260/465 D; 564/218; 564/223; 564/414
[58] Field of Search .................. 260/465 D; 564/221, 564/218, 223, 414

[56] References Cited

U.S. PATENT DOCUMENTS

| | | | |
|---|---|---|---|
| 2,924,620 | 2/1960 | Miller | 260/562 P X |
| 2,961,465 | 11/1960 | Contois, Jr. | 260/562 P X |
| 3,830,842 | 8/1974 | Yale | 260/562 P |
| 3,950,377 | 4/1976 | Barlow | 260/576 X |
| 4,117,167 | 9/1978 | Barlow et al. | 260/576 X |
| 4,128,665 | 12/1978 | Hunt et al. | 260/576 X |

FOREIGN PATENT DOCUMENTS

| | | | |
|---|---|---|---|
| 868165 | 5/1961 | United Kingdom | 260/576 |
| 1218965 | 1/1971 | United Kingdom | 260/576 |
| 1383523 | 2/1975 | United Kingdom | 260/576 |
| 1455207 | 11/1976 | United Kingdom | 260/576 |

OTHER PUBLICATIONS

Rondestvedt, Jr., Synthesis of 4-Aminodiphenylamine and Its Relatives, J. Org. Chem., vol. 42, No. 10, p. 1786 (1977).

*Primary Examiner*—Arthur P. Demers
*Attorney, Agent, or Firm*—Cushman, Darby & Cushman

[57] ABSTRACT

N-formyl anilino aromatic compounds containing two electronegative groups in the benzene ring, their manufacture from formanilides and aromatic halogen compounds and their use as intermediates for the manufacture of the corresponding diphenylamine compounds. The compounds are useful as pesticides.

8 Claims, No Drawings

ANILINE DERIVATIVES

This is a continuation of application Ser. No. 935,498, filed Aug. 18, 1978, now abandoned.

This invention relates to new aniline derivatives, and to a process for their manufacture and more particularly relates to new formanilido compounds and their manufacture and use as intermediates for the manufacture of N-phenyl aromatic amino compounds.

The manufacture of 4-nitro-N-formyldiphenylamine by treatment of 4-nitrodiphenylamine with formic-acetic anhydride is disclosed in the Journal of Organic Chemistry, Volume 42 at page 1787. However, the corresponding treatment of diphenylamines containing more than one electron-withdrawing substituent does not appear to lead to the formation of the N-formyl derivative.

The above-mentioned reference is part of an article describing the manufacture of 4-nitrodiphenylamine and certain derivatives by heating a mixture of the sodium derivative of formanilide with p-nitrochlorobenzene or the appropriate derivatives of these reactants in a solvent at temperatures of the order of 150° C. The article states that the corresponding formyl derivative could not be detected in the crude product of reaction.

It has now been found that the formyl derivatives of aromatic primary amines react very readily with benzene halides containing at least two electron-withdrawing substituents in the presence of acid-binding agents. The product obtained can be the N-phenyl-N-formyl derivative of the aromatic amine or is alternatively the N-phenyl derivative, apparently obtained from the N-formyl compound by loss of carbon monoxide (decarbonylation), or in some cases can be a mixture of the two. The temperature of reaction appears to play an important part in the nature of the product; furthermore, the N-formyl derivative can be converted to the N—H product by gentle heating so that it is probable that a "temperature of decarbonylation" exists.

Thus according to one feature of the invention, there are provided the formanilido compounds of the formula:

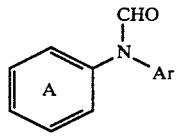  (1)

wherein Ar is an aromatic radical and the benzene ring A contains at least two electron-withdrawing substituents and which may be further substituted.

Also according to a further feature of the invention there is provided a process for manufacture of the formanilido compounds of formula (1) which comprises reacting together one mole of the N-formyl derivative of an aromatic amine, having the formula:

Ar.NH.CHO  (2)

with one mole of an aromatic halide of the formula:

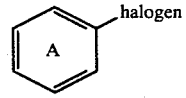  (3)

in which the benzene ring A is substituted as stated above, in the presence of a diluent and in the presence of an acid-binding agent, whilst maintaining the reaction temperature below that which causes decarbonylation.

According to yet a further feature of the invention, there is provided a process for manufacture of diphenylamine compounds of the formula:

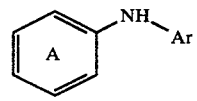  (4)

wherein Ar is an aromatic radical and the benzene ring A is substituted as stated above, which comprises heating a compound of formula (1) above the temperature of decarbonylation or reacting together one mole of the N-formyl derivative of an aromatic amine of formula (2) above, with one mole of an aromatic halide of formula (3) above in the presence of a diluent and in the presence of an acid-binding agent, whilst maintaining the reaction temperature above the temperature of decarbonylation of the corresponding compound of formula:

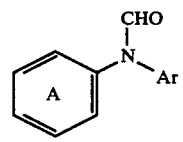  (1)

In the above formulae, the symbol Ar may represent a heterocyclic radical, e.g. a radical of the furane, thiophene, pyrimidine or pyridine series, which may be substituted, e.g. by halogen atoms, e.g. by chlorine or fluorine atoms; preferably, however, the symbol Ar represents a carbocyclic radical, more especially a radical of the naphthalene or, above all, the benzene series which may be substituted, e.g. by alkyl or alkoxy groups, preferably $C_1$ to $C_6$ alkyl or alkoxy, halogen, e.g. F, Cl or Br, $CF_3$ or CN.

The benzene ring A is substituted by at least two electron-withdrawing substituents; as examples of these, there may be mentioned CN, alkyl- or aryl-sulphonyl, alkyl- or aryl-carbonyl, but more especially $CF_3$ and $NO_2$. Preferably these substituents are present in the ortho and para positions to the nitrogen atom in the compounds of formula (1) and (4) and correspondingly to the halogen atom in the compounds of formula (3). However the benzene ring may contain other substituents which, when electron-withdrawing, are preferably also in the ortho or para position; other substituents e.g., halogen, or nucleophilic substituents, e.g. amino or substituted amino, etherified hydroxyl and etherified mercaptan, are preferably in the meta position or positions to the nitrogen atom of the compounds of formulae (1) and (3).

As specific examples of compounds of formula (1), there may be mentioned:
N-formyl-2-methyl-3-(2,4-dinitroanilino)furane, N-formyl-3-(2-nitro-4-trifluoromethylanilino)thiophene,
N-formyl-4-(2,4-dinitro-5-trifluoromethyl)anilino pyrimidine,
N-formyl-4-(2,5-dinitroanilino)-3,5-dichloro-2,6-difluoropyrimidine,
N-formyl-4-(2,5-dinitro-3-methoxyanilino)-3,5-dichloro-2-fluoro-6-methoxypyridine,
N-formyl-1-(2-nitro-4-cyano-5-methylanilino)-4,8-dichloronaphthalene,
N-formyl-1-(2,6-dinitroanilino)-2,4-dichloronaphthalene, and
N-formyl-2,4-dinitrodiphenylamine.

As preferred compounds of formula (1) however, there may be mentioned those of the formula:

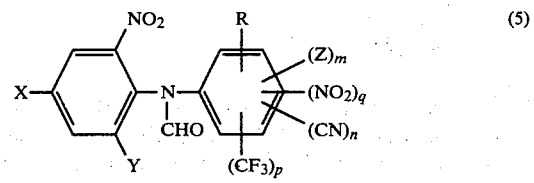

wherein one of X and Y is $NO_2$ and the other is $CF_3$, Z is halogen, preferably Cl, R is hydrogen or an alkyl or alkoxy group containing from 1 to 6 carbon atoms, $m=0-3$, $n=0$ or 1, $p=0-2$, $q=0-2$ and $m+n+p+q=1-3$, e.g.

N-formyl-2-(2-chloro-5-methylanilino)-3,5-dinitrobenzotrifluoride
N-formyl-4-(2,4,6-trichloroanilino)-3,5-dinitrobenzotrifluoride
N-formyl-2-(2,6-dichloroanilino)-3,5-dinitrobenzotrifluoride
N-formyl-4-(2nitroanilino)-3,5-dinitrobenzotrifluoride
N-formyl-2-(2,5-dichloroanilino)-3,5-dinitrobenzotrifluoride
N-formyl-4-(3-trifluoromethylanilino)-3,5-dinitrobenzotrifluoride
N-formyl-2-(2,4-dinitroanilino)-3,5-dinitrobenzotrifluoride
N-formyl-4-(3-nitroanilino)-3,5-dinitrobenzotrifluoride
N-formyl-2-(3-cyanoanilino)-3,5-dinitrobenzotrifluoride
N-formyl-4-(2-fluoroanilino)-3,5-dinitrobenzotrifluoride
N-formyl-2-(3-iodoanilino)-3,5-dinitrobenzotrifluoride
N-formyl-4-(4-iodoanilino)-3,5-dinitrobenzotrifluoride
N-formyl-2-(4-bromo-2-chloroanilino)-3,5-dinitrobenzotrifluoride
N-formyl-4-(4-bromo-3-methylanilino)-3,5-dinitrobenzotrifluoride
N-formyl-2-(2-bromo-4-methyl-6-nitroanilino)3,5-dinitrobenzotrifluoride
N-formyl-4-(2,4,5-trichloroanilino)-3,5-dinitrobenzotrifluoride
N-formyl-2-(2-chloroanilino)-3,5-dinitrobenzotrifluoride
N-formyl-4-(2-bromoanilino)-3,5-dinitrobenzotrifluoride
N-formyl-2-(4-fluoro-2-methylanilino)-3,5-dinitrobenzotrifluoride
N-formyl-4-(4-bromo-3-trifluoromethylanilino)-3,5-dinitrobenzotrifluoride
N-formyl-2-(2-nitro-4-trifluoromethylanilino)-3,5-dinitrobenzotrifluoride
N-formyl-4-(2,6-dichloro-4-nitroanilino)-3,5-dinitrobenzotrifluoride
N-formyl-2-(2-cyano-4-nitroanilino)-3,5-dinitrobenzotrifluoride
N-formyl-4-(4-chloro-2-nitroanilino)-3,5-dinitrobenzotrifluoride
N-formyl-2-(6-chloro-2,4-dinitroanilino)-3,5-dinitrobenzotrifluoride
N-formyl-4-(6-bromo-4-chloro-2-nitroanilino)-3,5-dinitrobenzotrifluoride
N-formyl-2-(4-bromo-2-nitroanilino)-3,5-dinitrobenzotrifluoride
N-formyl-4-(6-chloro-2-nitro-4-trifluoromethylanilino)3,5-nitrobenzotrifluoride
N-formyl-2(4,6-dichloro-2-nitroanilino)-3,5-dinitrobenzotrifluoride
N-formyl-4-(4-bromo-6-chloro-2-nitroanilino)-3,5-dinitrobenzotrifluoride
N-formyl-2-(3,5-bistrifluoromethylanilino)-3,5-dinitrobenzotrifluoride
N-formyl-4-(2-bromo-4-nitroanilino)-3,5-dinitrobenzotrifluoride
N-formyl-2-(2,4-dichloroanilino)-3,5-dinitrobenzotrifluoride
N-formyl-4-(3,4-dichloroanilino)-3,5-dinitrobenzotrifluoride
N-formyl-2-(3,5-dichloroanilino)-3,5-dinitrobenzotrifluoride
N-formyl-4-(2-chloro-4-nitroanilino)-3,5-dinitrobenzotrifluoride
N-formyl-2-(2,4,6-tribromoanilino)-3,5-dinitrobenzotrifluoride
N-formyl-4-(4-chloro-2-trifluoromethylanilino)-3,5-dinitrobenzotrifluoride
N-formyl-2-(4-methyl-2-nitroanilino)-3,5-dinitrobenzotrifluoride
N-formyl-4-(6-methyl-2-nitroanilino)-3,5-dinitrobenzotrifluoride
N-formyl-2-(4,5-dichloro-2-nitroanilino)-3,5-dinitrobenzotrifluoride
N-formyl-4-(3-chloro-4-cyanoanilino)-3,5-dinitrobenzotrifluoride
N-formyl-2-(3-chloro-4-fluoroanilino)-3,5-dinitrobenzotrifluoride
N-formyl-4-(4-chloro-3-nitroanilino)-3,5-dinitrobenzotrifluoride
N-formyl-2-(2-chloro-5-nitroanilino)-3,5-dinitrobenzotrifluoride
N-formyl-4-(3-chloro-5-methoxyanilino)-3,5-dinitrobenzotrifluoride
N-formyl-2-(2-fluoro-5-nitroanilino)-3,5-dinitrobenzotrifluoride
N-formyl-4-(4-chloro-2-methylanilino)-3,5-dinitrobenzotrifluoride
N-formyl-2-(2,4-difluoroanilino)-3,5-dinitrobenzotrifluoride
N-formyl-4-(4-chloro-3-trifluoromethylanilino)-3,5-dinitrobenzotrifluoride
N-formyl-2-(3-chloro-4-methylanilino)-3,5-dinitrobenzotrifluoride
N-formyl-4-(4-nitro-3-trifluoromethylanilino)-3,5-dinitrobenzotrifluoride
N-formyl-2-(2-methyl-5-nitroanilino)-3,5-dinitrobenzotrifluoride
N-formyl-4-(4-fluoro-3-methylanilino)-3,5-dinitrobenzotrifluoride
N-formyl-2-(2-methyl-4-nitroanilino)-3,5-dinitrobenzotrifluoride N-formyl-4-(2,3-dichloroanilino)-3,5-dinitrobenzotrifluoride
N-formyl-2-(2-fluoro-4-methylanilino)-3,5-dinitrobenzotrifluoride
N-formyl-4-(2,5-difluoroanilino)-3,5-dinitrobenzotrifluoride
N-formyl-2-(2-methoxy-4-nitroanilino)-3,5-dinitrobenzotrifluoride
N-formyl-4-(2,5-dichloro-4-nitroanilino)-3,5-dinitrobenzotrifluoride
N-formyl-2-(2,4-dibromoanilino)-3,5-dinitrobenzotrifluoride
N-formyl-4-(2,6-dibromoanilino)-3,5-dinitrobenzotrifluoride
N-formyl-2-(2,5-dibromoanilino)-3,5-dinitrobenzotrifluoride
N-formyl-2-(4-nitroanilino)-3,5-dinitrobenzotrifluoride
N-formyl-4-(4-cyanoanilino)-3,5-dinitrobenzotrifluoride
N-formyl-2-(3-chloroanilino)-3,5-dinitrobenzotrifluoride
N-formyl-4-(4-bromoanilino)-3,5-dinitrobenzotrifluoride
N-formyl-2-(2-bromo-5-trifluoromethylanilino)-3,5-dinitrobenzotrifluoride
N-formyl-4-(2-cyanoanilino)-3,5-dinitrobenzotrifluoride
N-formyl-2-(3-bromoanilino)-3,5-dinitrobenzotrifluoride
N-formyl-4-(4-bromo-2-methylanilino)-3,5-dinitrobenzotrifluoride
N-formyl-2-(5-chloro-2-trifluoromethylanilino)-3,5-dinitrobenzotrifluoride
N-formyl-2-(2-chloro-4-methylanilino)-3,5-dinitrobenzotrifluoride
N-formyl-4-(2-bromo-4-methylanilino)-3,5-dinitrobenzotrifluoride
N-formyl-2-(4-fluoro-2-nitroanilino)-3,5-dinitrobenzotrifluoride
N-formyl-4-(2-methoxy-5-nitroanilino)-3,5-dinitrobenzotrifluoride.

As examples of compounds of formula (2), there may be mentioned:
formanilide
o-, m- and p-methyl-formanilides
o-, m- and p-chloroformanilides
o-, m- and p-bromoformanilides
o-, m- and p-nitroformanilides
m- and p-cyanoformanilides
2,4- and 2,5-dicyanoformanilides
4-methanesulphonylformanilide
4-ethoxycarbonylformanilide
2,4-, 2,5- and 3,5-dichloroformanilides
2,4-, 2,5- and 3,5-dibromoformanilides
2-methyl-4- and 5-chloroformanilides
2-trifluoromethyl-4-chloroformanilide
2-chloro-5-trifluoromethylformanilide
2-cyano-4-chloroformanilide
2-methoxycarbonyl-4-chloro- and 4-nitroformanilides
2-bromo-4-nitroformanilide
2-chloro-4-ethoxyformanilide
2-chloro-4-methylsulphonylformanilide
2,3-dichloroformanilide
2,6-dichloroformanilide
2-trifluoromethylformanilide
2-methylsulphonyl-4-chloroformanilide
2,4-dinitro-6-methylsulphonylformanilide
2-methylsulphonyl-4-nitroformanilide
2,4-dinitroformanilide
2-cyano-4-methylsulphonylformanilide
2,6-dichloro-4-cyanoformanilide
2,6-dichloro-4-nitroformanilide
2,4-dinitro-6-chloroformanilide
2-cyano-4-nitroformanilide
2-formylaminothiazole
2-formylamino-5-nitrothiazole
3-formylaminopyridine
3-formylaminoquinaline
3-formylaminopyrazole
3-formylamino-1-phenylpyrazole, and
4-formylamino-5-methylpyrimidine.

As examples of compounds of formula (3), there may be mentioned:
2,4-, 2,5- and 2,6-dinitrochlorobenzenes
2,4,6-trinitrochlorobenzene
2,4-dinitro-6-trifluoromethylchlorobenzene
2,6-dinitro-4-trifluoromethylchlorobenzene
2-methoxycarbonyl-4-nitrochlorobenzene
2,4-dinitro-6-methylsulphonylchlorobenzene
2-methylsulphonyl-4-nitrochlorobenzene
2-cyano-4-nitrochlorobenzene, and
2-cyano-4-nitrochlorobenzene, and
4-chloro-2-nitrobenzophenone.

The new processes can conveniently be carried out by stirring a mixture of the compounds of formulae (2) and (3) in a diluent, the acid-binding agent also being present, or being added as reaction proceeds. As diluents, there may be used liquids, preferably of a polar nature which are inert to the reactants under the conditions used; more especially it is preferred to use liquids which are solvents for one or both of the reactants. As examples of preferred diluents, there may be mentioned polar aprotic liquids, hydroxyl compounds or ethers or polyethers. As examples of polar aprotic liquids which may be used, there may be mentioned dimethylsulphoxide, dimethylacetamide, and more especially dimethylformamide. As examples of hydroxyl compounds, there may be mentioned alkanols, preferably those containing 1 to 4 carbon atoms, especially ethanol. As examples of liquid ethers, hydroxyethers or polyethers which may be used, there may be mentioned diethyl ether, dioxan, tetrahydrofuran, $\beta$-ethoxyethanol, diethylene glycol, dipropylene glycol, polyethylene and polypropylene glycols of molecular weight 150 to 3000, also the monomethyl, or other monoalkyl, e.g. up to $C_8$, ethers of these polyether glycols. Water can be used as a diluent, preferably containing a small amount of a cationic surface-active agent or a water-miscible organic liquid, for example a water-miscible aprotic polar liquid, alkanol, ether or polyether of the kinds mentioned above.

As acid-binding agents, there may be used a wide range of alkaline substances, provided that they also are relatively inert to the reactants. Thus primary and secondary amines, also ammonia, which react readily with compounds of formula (3) are unsuitable, but tertiary amines e.g. triethylamine, can be used; it is preferred however to use an inorganic acid-binding agent, e.g. the carbonate or hydroxide of an alkaline earth metal or alkali-metal. The preferred acid-binding agent is potassium carbonate.

The amount of alkali metal carbonate used should be at least one mole per mole of halide or formylamino compound, and is preferably greater than this, e.g. from 2 to 3 moles per mole.

The reaction can be carried out at a temperature lying above or below that which gives rise to decarbonylation of the resulting formylamino compound, depending on the desired product. This temperature can easily be determined in practice by checking for the evolution of carbon monoxide from the reaction mixture by standard test methods, at various reaction temperatures.

The new formanilido compounds are pesticides themselves and are valuable intermediates for conversion to the N-phenyl aromatic amino compounds of formula (4), which are difficult to synthesise by the direct reaction of amine and halogen compounds and which in many cases are even more valuable for use as pesticides.

The invention is illustrated by the following Examples in which parts and percentages are by weight:

EXAMPLE 1

A mixture of 541 parts of 2-chloro-3,5-dinitrotrifluoromethylbenzene, 447 parts of 2-chloro-5-trifluoromethylformanilide, 820 parts of potassium carbonate and 2600 parts of dimethylformamide was stirred and heated at 40° C. for 3 hours. The mixture was poured into a mixture of water (27,000 parts) and hydrochloric acid, s.g. 1.18 (2360 parts) and the solid residue was filtered off, washed with water, dried and recrystallised from carbon tetrachloride to give N-formyl-2,4-dinitro-2'-chloro-5'6-bis(trifluoromethyl)diphenylamine as a pale yellow powder m.p. 140°–142° C.

EXAMPLE 2

The quantities of materials described in Example 1 were stirred and heated at 60° C. for 6 hours. 7000 parts of water and 2360 parts of hydrochloric acid, s.g. 1.18, were added and the mixture was poured into 20,000 parts of water. The solid product was filtered off and dried to give 740 parts of a yellow powder m.p. 115° C. (89% yield).

By washing this product with a small amount of ethanol, 600 parts of material of m.p. 140°–142° C. was obtained. Pure 2,4-dinitro-2'-chloro-5',6-bis(trifluoromethyl)diphenylamine has m.p. 142°–3° C.

By replacing the solvent used in Example 2 by those indicated in the following table, the result stated in the final column was obtained The "crude product" is usually a mixture of the diphenylamine and the formyl derivative.

| Example | Solvent | Result |
|---|---|---|
| 3 | dimethylsulphoxide | 28% yield of crude product |
| 4 | dimethylacetamide | 95% yield of crude product |
| 5 | Polyether (1) | 83% yield of pure amine |
| 6 | Polyether (2) | 82% yield of pure amine |
| 7 | polyethylene glycol MW 300 | 87% yield of crude product mp 139° C. |
| 8 | ethoxyethanol | 56% yield of crude product |
| 9 | dipropylene glycol | 79% yield of crude product. |

EXAMPLE 10

228 parts of 2,5-dichloroformanilide, 325 parts of 2-chloro-3,5-dinitrotrifluoromethylbenzene, 4920 parts of potassium carbonate, and 1560 parts of dimethylformamide were stirred together at 60° C. for 24 hours. 1410 parts of hydrochloric acid (s.g. 1.18) and 2500 parts of water were added and the mixture was poured into 12,000 parts of water. A tar was formed which when separated from the aqueous liquor and treated with 300 parts of ethanol gave 243 parts (51% theory) of a crystalline solid m.p. 122°–3° C. Pure 2',5'-dichloro-2,4-dinitro-6-trifluoromethyldiphenylamine melts at 128° C.

EXAMPLE 11

Example 10 was repeated but using only 200 parts of potassium carbonate and using 500 parts of polyethylene glycol of mol.wt. 300 in place of the dimethylformamide. After 3 hours at 60° C., the reaction was complete, but the product was found by thin-layer chromatography to by the N-formyl derivative of 2',5'-dichloro-2,4-dinitro-6-trifluoromethyldiphenylamine. The temperature was raised to 100° C. for 2 hours when evolution of carbon monoxide had ceased.

The product obtained by acidification and drowning into water weighed 3750 parts and was recrystallised from isopropanol to give 241 parts of 2',5'-dichloro-2,4-dinitro-6-trifluoromethyl diphenylamine, m.p. 127°–9° C.

EXAMPLE 12

541 parts of 2-chloro-3,5-dinitrotrifluoromethylbenzene and 447 parts of 2-chloro-5-trifluoromethylformanilide were stirred in 1000 parts of 50% aqueous ethanol and 820 parts of potassium carbonate were added as quickly as possible, keeping the temperature below 35° C. The mixture was stirred at 30°–35° C. for 4 hours then heated to reflux temperature and held at reflux for 2 hours until decarbonylation appeared to be complete.

The mixture was cooled, and the solid precipitate filtered off, washed with water and dried. 812 parts of a crude material were obtained, containing 95% by weight of the diphenylamine product; this is a 90% yield of the latter.

EXAMPLE 13

541 parts of 2-chloro-3,5-dinitrotrifluoromethylbenzene and 447 parts of 2-chloro-5-trifluoromethylformanilide were stirred in 1000 parts of water containing 60 parts of lauryl dimethylbenzyl ammonium chloride and 30 parts of polyglycerol recinoleate. A saturated solution of 820 parts of potassium carbonate in water is added as quickly as possible, keeping the temperature below 50° C., and the mixture is stirred at 50° C. for 4 hours.

1200 parts of ethanol are then added and the mixture is heated to reflux and stirred under reflux for 2 hours, when decarbonylation appears to be complete. The mixture is cooled and filtered and the residue is washed with water and dried.

836 parts of a crude material are obtained, containing 92.5% of the pure diphenylamine derivative, equivalent to a 90% yield of the latter.

I claim:

1. A formanilido compound of the formula:

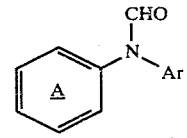

wherein Ar is an aromatic radical and the benzene ring A contains at least two electron-withdrawing substituents and may be further substituted by methyl or methoxy.

2. A formanilido compound as claimed in claim 1 wherein Ar is a radical of the benzene series.

3. A formanilido compound as claimed in claim 2 wherein the radical Ar carries at least one substituent selected from the group consisting of F, Cl, Br, $CF_3$, CN and alkyl or alkoxy groups containing from 1 to 6 carbon atoms.

4. A formanilido compound as claimed in claim 1 wherein the electron-withdrawing substituents in benzene ring A are present in the ortho- and para- positions to the nitrogen atom.

5. A formanilido compound as claimed in claim 1 and having the formula:

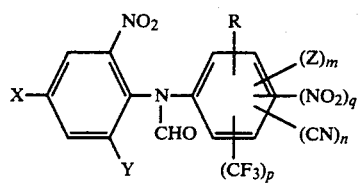

wherein one of X and Y is $NO_2$ and the other is $CF_3$, Z is halogen, R is hydrogen or an alkyl or alkoxy group containing from 1 to 6 carbon atoms, $m=0-3$, $n=0$ or 1, $p=0-2$ and $m+n+p+q=1-3$.

6. A formanilido compound as claimed in claim 5 wherein Z is chlorine.

7. A process for the manufacture of the formanilido compounds claimed in claim 1 which comprises reacting together one mole of the N-formyl derivative of an aromatic amine having the formula:

Ar—NH.CHO with one mole of an aromatic halide of the formula:

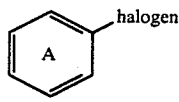

wherein Ar has the meaning stated in claim 1 and the benzene ring A is substituted as stated in claim 1, in the presence of a diluent and in the presence of an acid-binding agent, whilst maintaining the reaction temperature below that which causes decarbonylation.

8. A process for the manufacture of diphenylamine compounds of the formula:

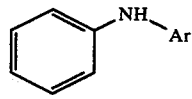

wherein Ar has the meaning stated in claim 1 and the benzene ring A is substituted as stated in claim 1, which comprises heating a compound of the formula:

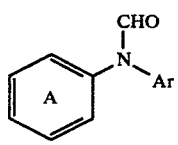

above the temperature of decarbonylation.
or reacting together one mole of the N-formyl derivative of an aromatic amine having the formula:

Ar.NH.CHO with one mole of an aromatic halide of the formula:

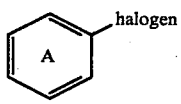

in the presence of a diluent and in the presence of an acid-binding agent, whilst maintaining the reaction temperature above the temperature of decarbonylation of the corresponding compound of formula:

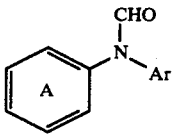

* * * * *